(12) United States Patent
Capote (10) Patent No.: US 12,076,056 B2
(45) Date of Patent: Sep. 3, 2024

(54) BONE ANCHOR

(71) Applicant: Zimmer Biomet Spine, Inc., Westminster, CO (US)

(72) Inventor: Allison Christine Capote, Boulder, CO (US)

(73) Assignee: Zimmer Biomet Spine, Inc., Westminster, CO (US)

(*) Notice: Subject to any disclaimer, the term of this patent is extended or adjusted under 35 U.S.C. 154(b) by 71 days.

(21) Appl. No.: 17/560,962

(22) Filed: Dec. 23, 2021

(65) Prior Publication Data

US 2022/0110663 A1 Apr. 14, 2022

Related U.S. Application Data (63) Continuation of application No. 16/550,637, filed on Aug. 26, 2019, now Pat. No. 11,241,259.

(60) Provisional application No. 62/724,811, filed on Aug. 30, 2018.

(51) Int. Cl.
*A61B 17/70* (2006.01)
*A61B 17/86* (2006.01)

(52) U.S. Cl.
CPC ...... *A61B 17/7038* (2013.01); *A61B 17/7032* (2013.01); *A61B 17/7034* (2013.01); *A61B 17/7037* (2013.01); *A61B 17/8685* (2013.01)

(58) Field of Classification Search
CPC ............ A61B 17/7038; A61B 17/7032; A61B 17/7034; A61B 17/7035; A61B 17/70347; A61B 17/704
See application file for complete search history.

(56) References Cited

U.S. PATENT DOCUMENTS

| | | | |
|---|---|---|---|
| 7,875,065 | B2 | 1/2011 | Jackson |
| 9,168,069 | B2 | 10/2015 | Jackson et al. |
| 9,603,630 | B2 | 3/2017 | Farris |
| 9,763,700 | B1 | 9/2017 | Gregory |
| 9,820,782 | B2 | 11/2017 | Daniels |
| 9,924,971 | B2 | 3/2018 | Biedermann et al. |
| 10,034,691 | B1 | 7/2018 | Lish |
| 2004/0236330 | A1 | 11/2004 | Purcell et al. |
| 2005/0283157 | A1 | 12/2005 | Coates et al. |
| 2007/0088357 | A1 | 4/2007 | Johnson et al. |
| 2008/0154315 | A1 | 6/2008 | Jackson et al. |
| 2008/0161859 | A1 | 7/2008 | Nilsson |

(Continued)

FOREIGN PATENT DOCUMENTS

| | | |
|---|---|---|
| EP | 2964115 A1 | 1/2016 |

OTHER PUBLICATIONS

Corrected Notice of Allowance for U.S. Appl. No. 16/550,637, dated Dec. 27, 2021 3 pages.

(Continued)

*Primary Examiner* — Ellen C Hammond
*Assistant Examiner* — Holly Joanna Lane
(74) *Attorney, Agent, or Firm* — Sheridan Ross P.C.

(57) ABSTRACT

An anchor assembly can be couplable to a bone and can include an anchor and a housing. The anchor can include a shank securable to bone and a head coupled to a proximal portion of the shank. The housing can include a proximal portion including an anchor bore and a distal portion including a secondary bore configured to engage the anchor to limit angulation of the anchor relative to the housing.

20 Claims, 9 Drawing Sheets

(56) References Cited

U.S. PATENT DOCUMENTS

| | | | |
|---|---|---|---|
| 2011/0178559 A1* | 7/2011 | Barry | A61B 17/8605 606/305 |
| 2011/0202094 A1 | 8/2011 | Pereira et al. | |
| 2012/0016425 A1 | 1/2012 | Shaffrey et al. | |
| 2012/0059426 A1* | 3/2012 | Jackson | A61B 17/7076 606/300 |
| 2014/0257411 A1 | 9/2014 | Rezach | |
| 2015/0282844 A1* | 10/2015 | Vedula | A61B 17/7032 606/305 |
| 2015/0297266 A1 | 10/2015 | Kirschman | |
| 2016/0331412 A1 | 11/2016 | Biedermann et al. | |
| 2017/0135732 A1 | 5/2017 | Jackson et al. | |
| 2017/0245898 A1 | 8/2017 | May et al. | |
| 2017/0333085 A1 | 11/2017 | Jackson et al. | |
| 2019/0029731 A1* | 1/2019 | Shoshtaev | A61B 17/861 |
| 2020/0069344 A1 | 3/2020 | Capote | |
| 2020/0229847 A1* | 7/2020 | Capote | A61B 17/8625 |
| 2022/0313320 A1* | 10/2022 | Jackson | A61B 17/863 |

OTHER PUBLICATIONS

U.S. Appl. No. 16/550,637, filed Aug. 26, 2019, Bone Anchor.

U.S. Appl. No. 16/694,098, filed Nov. 25, 2019, Bone Anchor.

"U.S. Appl. No. 16/550,637, Final Office Action mailed Apr. 7, 2021", 11 pgs.

"U.S. Appl. No. 16/550,637, Non Final Office Action mailed Jan. 13, 2021", 24 pgs.

"U.S. Appl. No. 16/550,637, Non Final Office Action mailed Jul. 7, 2021", 10 pgs.

"U.S. Appl. No. 16/550,637, Advisory Action mailed Jun. 2, 2021", 3 pgs.

"U.S. Appl. No. 16/550,637, Examiner Interview Summary mailed Aug. 31, 2021", 2 pgs.

"U.S. Appl. No. 16/550,637, Notice of Allowance mailed Nov. 18, 2021", 5 pgs.

"U.S. Appl. No. 16/550,637, Response filed Mar. 8, 2021 to Non Final Office Action mailed Jan. 13, 2021", 17 pgs.

"U.S. Appl. No. 16/550,637, Response filed May 20, 2021 to Final Office Action mailed Apr. 7, 2021", 13 pgs.

"U.S. Appl. No. 16/550,637, Response filed Sep. 20, 2021 to Non Final Office Action mailed Jul. 7, 2021", 12 pgs.

"U.S. Appl. No. 16/694,098, Final Office Action mailed Sep. 24, 2021", 11 pgs.

"U.S. Appl. No. 16/694,098, Non Final Office Action mailed Apr. 30, 2021", 11 pgs.

"U.S. Appl. No. 16/694,098, Response filed Jun. 17, 2021 to Non Final Office Action mailed Apr. 30, 2021", 10 pgs.

"European Application Serial No. 19194424.8, Extended European Search Report mailed Jan. 23, 2020", 10 pgs.

"European Application Serial No. 19194424.8, Response filed Sep. 4, 2020 to Extended European Search Report mailed Jan. 23, 2020", 18 pgs.

"European Application Serial No. 20152733.0, Extended European Search Report mailed Jun. 19, 2020", 9 pgs.

"European Application Serial No. 20152733.0, Response filed Jan. 22, 2021 to Extended European Search Report mailed Jun. 19, 2020", 16 pgs.

* cited by examiner

BONE ANCHOR

CLAIM OF PRIORITY

This application is a continuation of U.S. patent application Ser. No. 16/550,637, filed on Aug. 26, 2019, which claims the benefit of U.S. Provisional Patent Application Ser. No. 62/724,811, filed on Aug. 30, 2018, the benefit of priority of each of which is claimed hereby, and each of which is incorporated by reference herein in its entirety.

BACKGROUND

This document pertains generally, but not by way of limitation, to systems and methods for fixation of bones during orthopedic procedures. More particularly, this disclosure relates to, but not by way of limitation, vertebral bone anchors. Orthopedic devices such as rods, plates, tethers, staples, and other devices can be used in various spinal procedures to correct abnormalities (e.g., scoliosis) or to address injuries (e.g., vertebral fracture). In some spinal procedures, anchors and rods can be secured along a vertebral column to vertebrae to stabilize a region of the spine. In these procedures, pedicle screws (or vertebral anchors) can be secured to individual vertebra and tied together with a connecting rod.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Bone anchors can be used together with connecting members (such as rigid and semi-rigid rods) to straighten a region of a human spine to address an abnormality (e.g., scoliosis), to stabilize a spine following an injury (e.g., fractured vertebrae), or to address degeneration of the spine caused by disease. In one example procedure, anchors are driven into vertebrae and are manipulated from outside of the cavities. The housing of the anchor can be positioned with respect to the shank of the anchor and the housings can be individually and collectively positioned along the spinal column to receive a connecting rod. The connecting rod can extend through two or more housings and can be secured to each housing by a closure top or set screw.

In some procedures, disruption of muscle around the vertebral column may be reduced by using a technique that secures vertebral anchors along a cortical trajectory. That is, the trajectory along which the shank of the anchor extends into the vertebra to which it is secured can be through primarily cortical bone as opposed to a standard trajectory where the shank can extend into the vertebral body. In addition to helping to limit muscle disruption, this technique may enable use of smaller diameter and length anchors while maintaining good fixation. However, to allow for proper support of the connecting member to the housing, the cortical trajectory can require relatively larger angulation of the shank relative to the housing of the anchor in the medial to lateral and/or caudal to cranial directions. Further, because these procedures are performed with relative little work space (within a retracted opening), it is desirable to achieve relatively large angulation at multiple positions of the shank relative to the housing while still retaining the shank within the housing.

This disclosure addresses these problems by including rounded notches in a distal end of the housing. More specifically, to provide the angulation required for use of a cortical trajectory, this disclosure proposes to use a secondary bore in the anchor housing that includes, in one example, rounded notches or corners configured to allow for a relatively high degree of angulation of the anchor relative to the housing to allow the cortical trajectory to be used while still allowing the housings to be aligned to accept a connecting rod.

Also, in some examples, the anchor housing can include multiple rounded notches in a symmetrical arrangement (such as a square shape with rounded corners from a distal perspective). This can allow the housing to be positioned at the required angulation relative to the anchor when the housing in in multiple positions, helping to reduce a requirement of orienting the housing relative to the anchor, which can save time and energy during a procedure.

This discussion is intended to provide an overview of subject matter of the present patent application. It is not intended to provide an exclusive or exhaustive explanation of the invention. The discussion below is included to provide further information about the present patent application.

Figure 1:
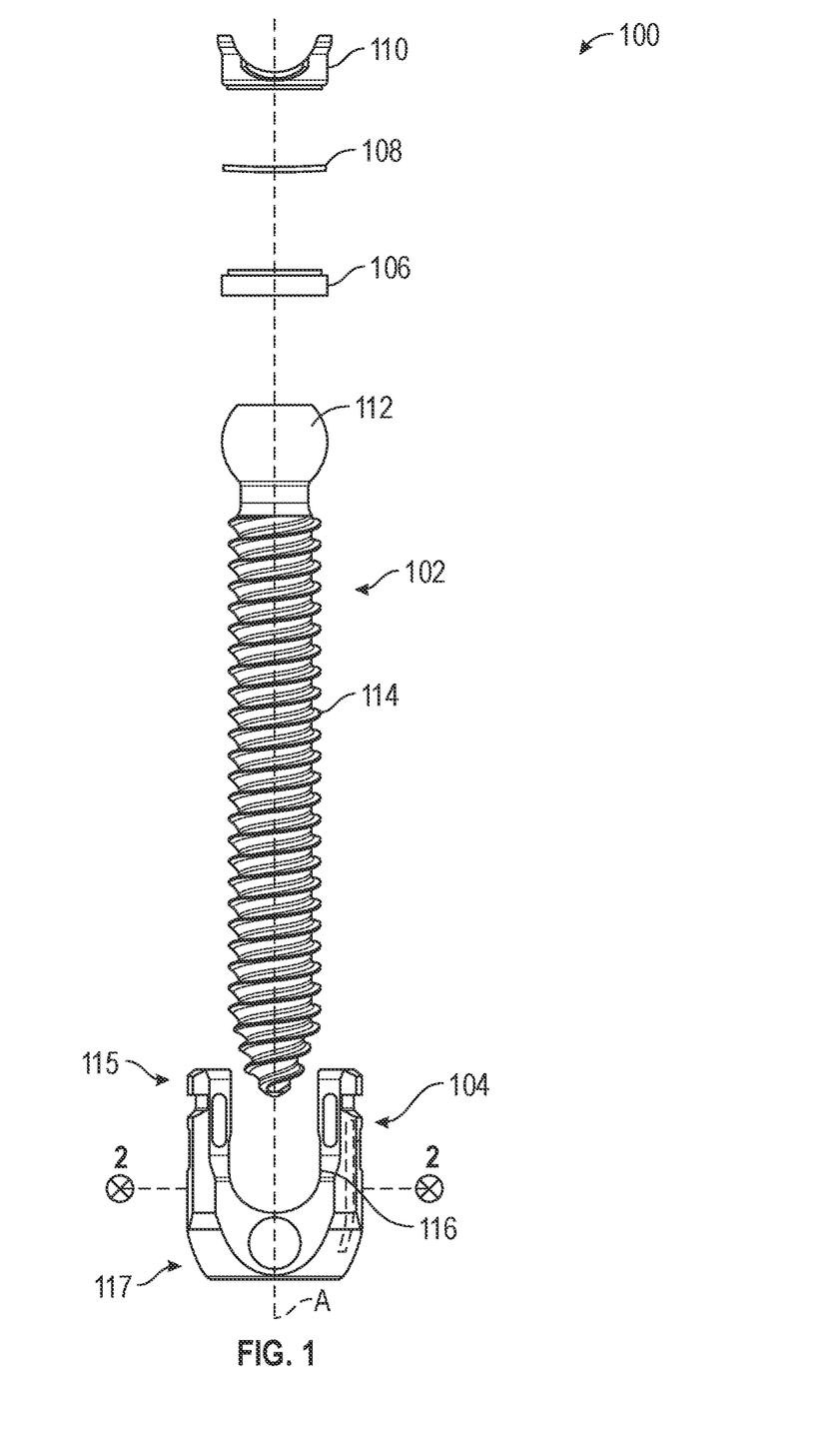
FIG. 1 illustrates an exploded view of an anchor assembly from an anterior perspective, in accordance with at least one example of this disclosure.

FIG. 1 illustrates an exploded view of an anchor assembly 100 from an anterior perspective, in accordance with at least one example of this disclosure. The anchor assembly 100 can include a housing and an anchor insertable through the housing and into bone for securing the anchor assembly 100 to a bone, in some examples.

The anchor assembly 100 can include an anchor 102, a housing 104, a lower piston 106, a biasing element 108, and an upper piston 110. The anchor 102 can include a head 112 and a shank 114. The housing 104 can include a proximal portion 115, an anchor bore 116, and a distal portion 117. Also shown in FIG. 1 are axis A and orientation indicators Proximal and Distal.

The anchor 102 can be a fastener configured to secure to a work piece, such as a bone, plate, prosthesis, or other device used in a surgery or operation. In other examples, the anchor 102 can be configured to engage wood, plastics, metals, and the like, for applications outside of surgical procedures. Anchor 102 can be comprised of plastics, metals, composites, combinations thereof, and the like. In some examples, the anchor 102 can be comprised of biocompatible materials such as such as stainless steels, cobalt-chromium, titanium variations, polyether ether ketone (PEEK), and combinations thereof.

The anchor 102 can include a head 112 located at a proximal portion of the anchor 102, which can connect to the shank 114. The head 112 can have a diameter larger than that of the shank 114 in some examples such that the shank 114 can extend through the housing 104 and so that the head 112 is limited from passing through a distal opening of the housing 104. The shank 114 can extend distally away from the head 112 and can include a threaded portion, in some examples, for engaging bone.

The housing 104 can include the proximal portion 115 connected the distal portion 117 with the anchor bore 116 extending through a proximal end of the proximal portion 115 along axis A and terminating within the distal portion 117. The anchor assembly 100 can be a top-loading assembly. The housing 104 can include a secondary opening to allow the shank 112 to extend through the housing but not the head 112. The housing 104 can thereby be configured to the head 112 in the housing 104.

The lower piston 106 can be a supporting member configured to engage the head 112 and to be supported thereby. The biasing element 108 can be a resilient element such as a spring. In some examples, the biasing element 108 can be a wave spring. In other examples, the biasing element 108 can be other springs or resilient members, such as a compression spring or compressible and resilient members comprised of materials such as rubbers, plastic, and the like. The upper piston 110 can be a supporting member configured to engage a proximal portion of the biasing element and configured to support a connecting member (shown in FIG. 2).

In assembly of some examples, the shank 114 of the anchor 102 can be inserted proximally-to-distally through the anchor bore 116 of the housing 104 such that the shank 114 extends distally out of the housing 104. The shank 114 can then be secured to a bone of a patient, as discussed below in further detail. A position of the housing 104 relative to the anchor 102 can be set during securing of the shank 114 into the bone. The position can be fixed by a force applied on the housing 104 by the head 112 when the shank 114 is secured to the bone.

Once the shank 114 is secured to the bone, the lower piston 106, the biasing element 108, and the upper piston 110 can be inserted into the anchor bore 116 such that the lower piston 106 engages the head 112. The biasing element 108 can be disposed between the lower piston 106 and the upper piston 110 to bias the upper piston 110 away from the lower piston. The upper piston 110 can receive the connecting member therein, which can be secured within the housing 104 by a closure top or set screw.

As discussed in further detail below, the secondary bore (or opening) in the distal portion 117 of the housing 104 can be configured to allow the anchor 102 to be oriented at various angles with respect to axis A and therefore relative to the housing 104. More accurately, when the anchor 102 is secured to bone, the housing 104 can be oriented at various positions relative to the anchor 102 and to the bone. In some examples, the housing 104 can allow for the anchor 102 to be positioned at relatively extreme angles (such as 30 degrees, 35 degrees, 40 degrees, and the like) with respect to axis A to allow for the anchor 102 to be secured to a vertebra using a cortical bone technique. Though this disclosure references use of anchor assembly 100 using a cortical trajectory technique, the anchor assembly 100 can be used in various other vertebral anchoring techniques where the benefits of the anchor assembly 100 (such as the anchor 102 can be oriented at various angles with respect to the housing 104) can be useful.

Figure 2:
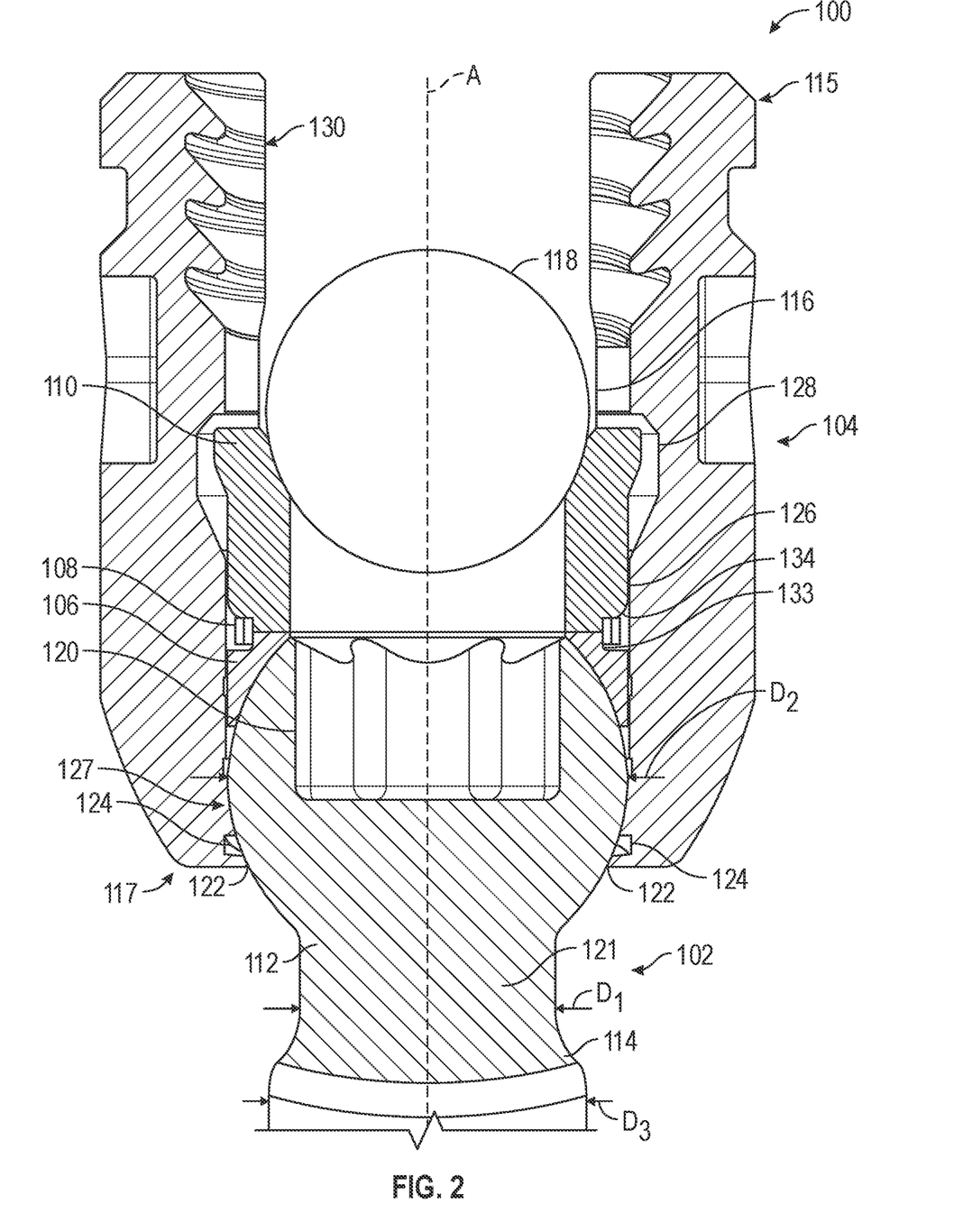
FIG. 2 illustrates a cross-sectional view of an anchor assembly across section 2-2 of FIG. 1, in accordance with at least one example of this disclosure.

FIG. 2 illustrates a cross-sectional view of the anchor assembly 100 across section 2-2 of FIG. 1, in accordance with at least one example of this disclosure. The anchor assembly 100 can include the anchor 102, the housing 104, the lower piston 106, the biasing element 108, the upper piston 110, and the connecting rod 118. The anchor 102 can include the head 112, the shank 114, a tool interface 120, and a neck 121. The housing 104 can include the proximal portion 115, the anchor bore 116, the distal portion 117, a secondary bore 122, the anchor threading (helical groove) 124, a head bore 126, a retaining portion 127, a piston bore 128, and closure top threading 130. The lower piston 106 can include a washer notch 133. The upper piston 110 can include a washer notch 134. Also shown in FIG. 2 are axis A, diameter D1, diameter D2, diameter D3, and orientation indicators Proximal and Distal.

Anchor assembly 100 of FIG. 2 can be consistent with anchor assembly 100 of FIG. 1, except that FIG. 2 shows additional details of anchor assembly 100. For example, FIG. 2 shows the tool interface 120 of head 112 which can be configured to interface with a tool and/or a tool bit to receive a torque from a tool to rotate the anchor 104 into and/or out of a bore (such as a bore in a vertebra).

FIG. 2 also shows that anchor 102 can include the neck 121, which can be a necked-down (or reduced diameter) portion of the anchor 104 connecting the head 112 to the shank 114. In some examples the neck 121 can have the diameter of D1, the head 112 can have the diameter D2, and the shank can have the diameter D3. The neck 121 can be positioned along the anchor 102 such that the neck 121 is the portion of the anchor 121 that contacts the distal portion 117 of the housing 104 to limit rotation or angulation of the anchor 102 with respect to (or relative to) the housing 104. Because the diameter D1 of the neck 121 is smaller than diameters D2 and D3, contact between the neck 121 and the distal portion 117 of the housing will occur at a greater angle of the anchor 102 with respect to axis A and the housing 104.

The housing 104 can also include the secondary bore 122, which can be an undercut, opening, or series of bevels at a distal end of the distal portion 117 of the housing 104. In some examples, the secondary bore 122 can be configured to contact the neck 121 to limit the angulation or relative angle of the anchor 102 with respect to the housing 104.

The housing 104 can also include the anchor threading (or helical groove) 124, which can be threading in the housing 104. The helical groove can be positioned in the housing 104 where the housing 104 tapers radially inward to create the retaining portion 127 (at the distal portion 117). The radially inward taper of the retaining portion 127 can be configured to retain the head 112 of the anchor 102 in the housing 104. Because the threading of the shank 114 can be as wide or wider than the head 112 of the anchor, anchor threading 124 can be required to allow the shank 114 to pass through the retaining portion 127 of the housing 104.

The head bore 126 of the housing 104 can be sized to allow the head 112 to pass through to the retaining portion 127 of the housing 104 where the head 112 can be retained. The head bore 126 can also be sized to retain the bottom piston 106 therein. The piston bore 128 can be sized to receive the top piston 110 in the housing, where the top piston includes a flared portion having a diameter larger than that of the bottom piston 106. The top piston 110 can be configured to support the connecting member 118 within the housing 104. The closure top threading 130 can be threading in housing 104 configured to threadably receive a closure top to secure the connecting member 118 within the anchor bore 116 of the housing 104.

The washer notch 133 of the lower piston 106 can be a notch or undercut in the lower piston 106 sized and shaped to partially retain the biasing element 108. Similarly, the washer notch 134 of the upper piston 110 can be a notch or undercut in the upper piston 110 sized and shaped to partially retain the biasing element 108. Together, the washer notches 133 and 134 and the housing bore 126 can contact the biasing element to retain the biasing element 108 between the lower piston 106 and the upper piston 110 to bias the upper piston 110 away from the lower piston.

Figures 3A, 3B:
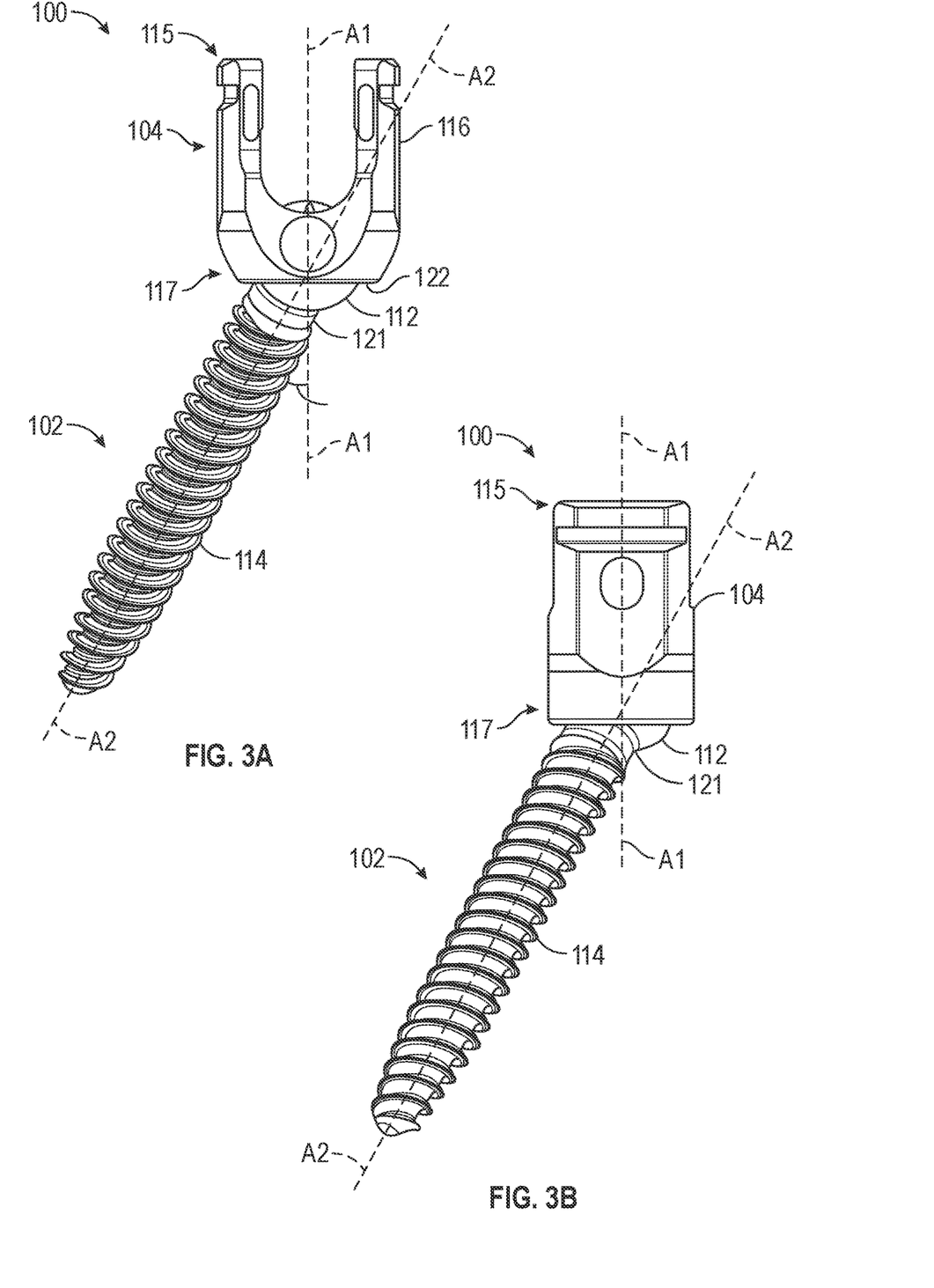
FIG. 3A illustrates an isometric view of an anchor assembly, in accordance with at least one example of this disclosure.
FIG. 3B illustrates an isometric view of an anchor assembly, in accordance with at least one example of this disclosure.
Figure 3C:
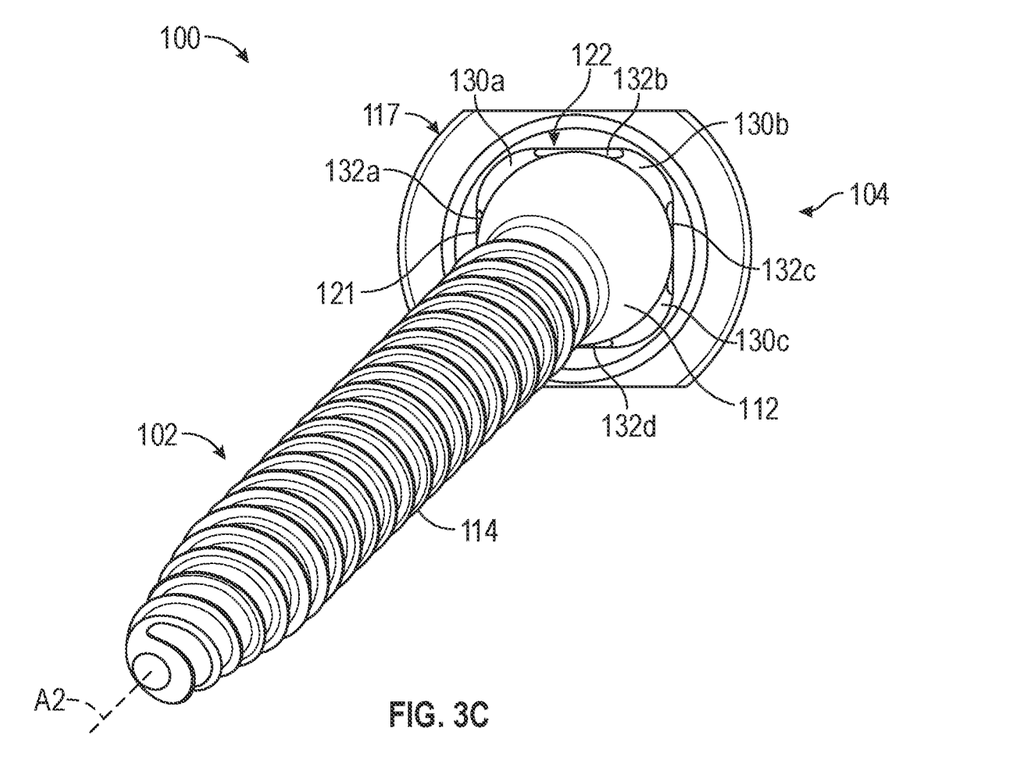
FIG. 3C illustrates an isometric view of an anchor assembly, in accordance with at least one example of this disclosure.

FIG. 3A illustrates an isometric view of the anchor assembly 100 from an anterior perspective, in accordance with at least one example of this disclosure. FIG. 3B illustrates an isometric view of the anchor assembly 100 from a lateral perspective, in accordance with at least one example of this disclosure. FIG. 3C illustrates an isometric view of an anchor assembly from a distal perspective, in accordance with at least one example of this disclosure. FIGS. 3A, 3B, and 3C are discussed below concurrently.

The anchor assembly 100 can include the anchor 102, and the housing 104. The anchor 102 can include the head 112, the shank 114, and the neck 121. The housing 104 can include the proximal portion 115, the anchor bore 116, the distal portion 117, and the secondary bore 122. The secondary bore 122 can include corner notches 130a-130d (a first angled notch 130a, a second angled notch 130b, a third angled notch 130c, and a fourth angled notch 130d; collectively referenced as corner notches 130) and straight portions 132a-132d (visible in FIG. 3C only and). Also shown in FIGS. 3A-3C are axis A1, axis A2, axis A3, angle Θ, and orientation indicators Proximal, Distal, Medial, Lateral, Anterior, and Posterior.

Anchor assembly 100 of FIGS. 3A-3C can be consistent with anchor assembly 100 of FIGS. 1 and 2, except that FIGS. 3A-3C show additional details of anchor assembly 100. For example, FIG. 3B shows how the neck 121 can contact the corner notch 130d of the secondary opening 122 to obtain the angle Θ of angulation of the anchor 102 with respect to the housing 104.

More specifically, the secondary opening 122 can include multiple edges, such as bevels, chamfers, J grooves, scotias, or the like. In some examples, the secondary opening can include corner notches 130a-130d which can each be rounded corner bevels, where each of the plurality of bevels curves along a face of each of the corner notches 130a-130d.

In some examples, each of the corner notches 130 can be connected by straight portions 132a-132d. In some examples, each of straight portions 132a-132d can be bevels in the secondary opening 122, each having a substantially flat or planar face. The first straight portion 132a can be connected to the first angled notch 130a and the second angled notch 130b; the second straight portion 132b can be connected to the second angled notch 130b and the third angled notch 130c; the third straight portion 132c can be connected to the third angled notch 130c and the fourth angled notch 130d; and, the fourth straight portion 132d can be connected to the first angled notch 130a and the fourth angled notch 130d.

This example of the secondary opening 122 can have a geometric shape substantially of a square with rounded corners from a distal perspective (as shown in FIG. 3C). As shown in FIGS. 3A-3C contact between the neck 121 and angled notch 130d can create an angulation of the shank 114 with respect to the housing 104 at the angle Θ, where the angle Θ is the angle between axis A1 (of the housing 104 and housing anchor bore 116) and axis A2 (extending along anchor 102). In some examples, the angle Θ can be 5, 10, 15, 20, 25, 30, 35, 40, 45, 50, 55 degrees, or the like (including degrees between values listed). The ability to provide the angle Θ at high angulation can allow for the anchor assembly 100 to be used in a procedure where the anchor 102 is installed using a cortical trajectory. Also, the anchor assembly 100 can be useful in various other vertebral anchor installation techniques where high angulation is desired or required.

Also, by providing four of curved notches 130a-130d, each capable of providing angulation at the angle Θ of the shank 114 relative to the housing 104 while still retaining the shank 114 within the housing 104, the anchor assembly 100 provides an anchor housing 104 that is symmetrical about two planes and therefore can be quickly positioned to a desired orientation during a procedure, helping to save the physician time and energy during what can be a relatively time-intensive procedure.

In the arrangement of this example, contact between the neck 121 and the straight portions (any of 132a-132d) can result in angulation of the anchor 102 with respect to the housing 104 at an angle that is lower than the angle Θ. In this example each of the angled notches 130a-130d can produce an angle Θ that is the same. In other examples, each of the angled notches 130a-130d can produce an angle Θ that is different.

Figure 4:
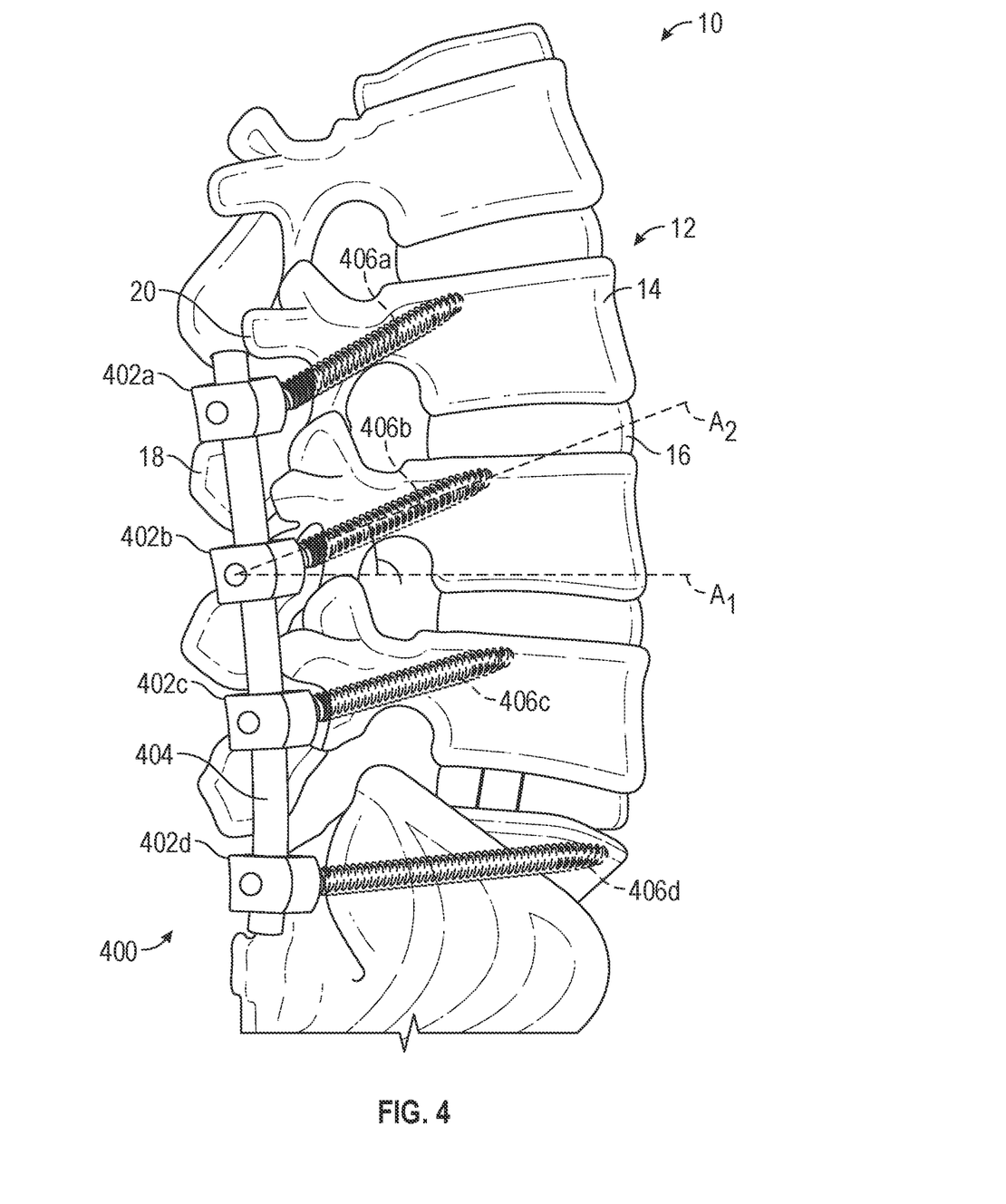
FIG. 4 illustrates a lateral view of a vertebral column and fixation assembly, in accordance with at least one example of this disclosure.

FIG. 4 illustrates a lateral perspective of a vertebral column 10 and a fixation assembly 400, in accordance with at least one example of this disclosure. In FIG. 4, the fixation assembly 400 can be secured to the vertebral column 10, as discussed in further detail below. Any of the previously discussed anchor assemblies can be secured to such a vertebral column.

Vertebral column 10 can include a vertebra 12, which can include a vertebral body 14, a disk 16, a spinous process 18, and a transverse process 20. The fixation assembly 400 can include housings 402a-402b, a connecting member 404, and anchors 406a-406d, where each of the housings 402a-402b corresponds to one of the anchors 406a-406d. Also shown in FIG. 4 are axis A1, axis A2, angle Θ, and orientation indicators Superior, Inferior, Anterior, and Posterior.

The fixation assembly 400 of FIG. 4 can operate consistently with the assemblies described in FIGS. 1-3C above, except that FIG. 4 shows the assembly 400 installed in vertebral column 10. As shown in FIG. 4, each of the anchors 406a-406d are secured to cortical bone of individual vertebra of the vertebral column 10.

When each of the anchors 406a-406d are installed within respective vertebrae using the cortical trajectory, the anchors 406a-406d may have a high degree of angulation with respect to their respective housings 402a-402d. For example, axis A1 can extend substantially through an anchor bore of housing 402b and axis A2 can extend substantially along a shank of the anchor 406b. The angle Θ can be formed by axes A1 and A2. In the example shown in FIG. 4, the angle Θ can represent a large angulation of the anchor 406b relative to the housing 402b in a inferior-to-superior direction, such as 35 degrees (or other angulations as described above). In some examples, anchor 406b can be positioned to create a large angulation relative to the housing 402b in a medial-to-lateral direction, such as 35 degrees (or other angulations as described above).

Because each of the housings 402a-402d can include rounded notches configured to allow for the relatively large angulations of the anchors 406a-406d relative to the housings 402a-402d, respectively, the housings 402a-402d can be aligned to allow the connecting member 404 to be relatively easily installed following installation of the anchors, which can save time and energy during a procedure.

FIG. 4 also shows that the anchors 406a-406d can be installed using different angulations. For example, the angulation of anchors 406d can be smaller than that of the anchor 406a. In this way, the housings 402a-402d can be used to create a variety of angulations of the anchors 406a-406d so that a single housing design can be used for multiple vertebral installations.

Figures 5A, 5B:
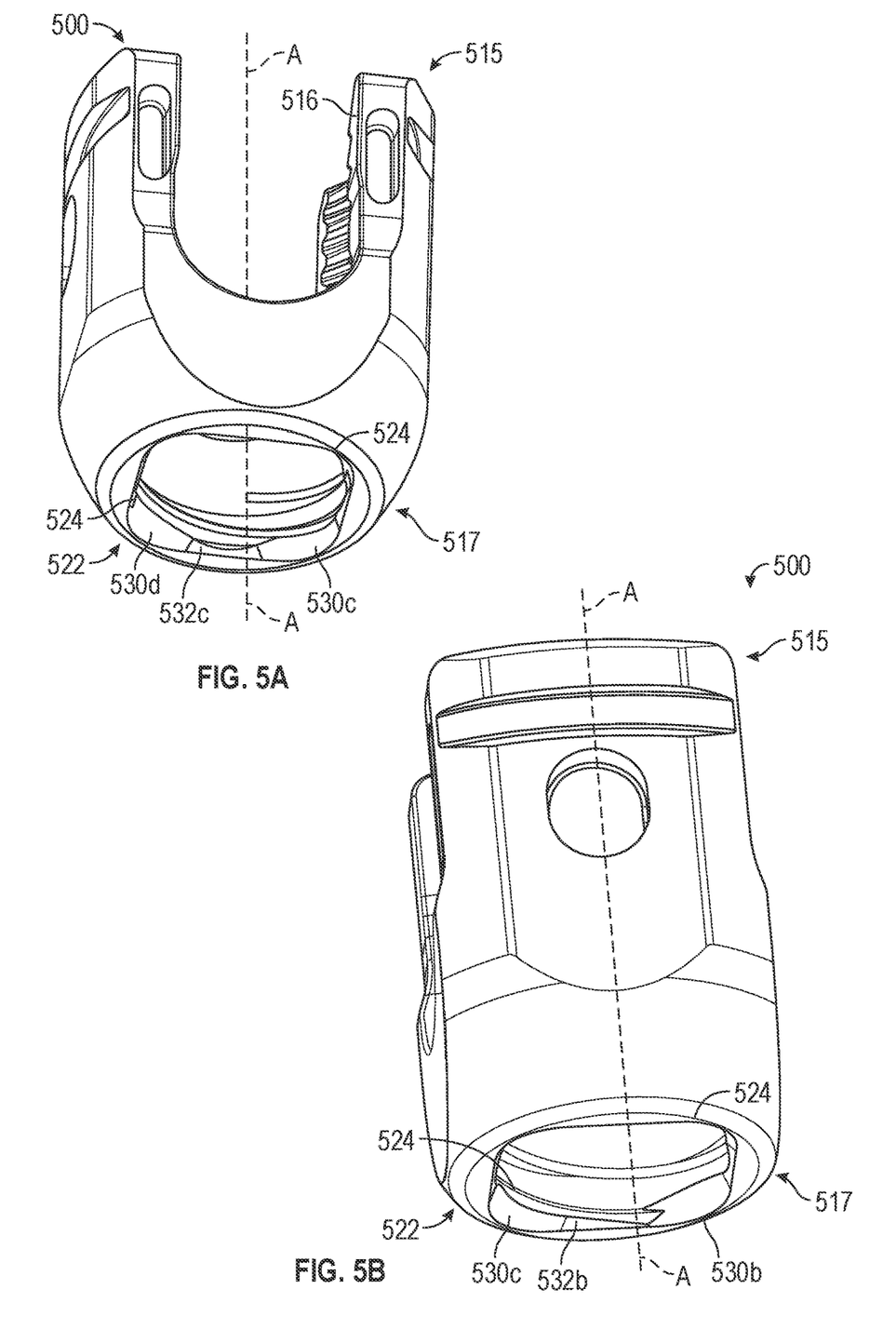
FIG. 5A illustrates an isometric view of an anchor housing, in accordance with at least one example of this disclosure.
FIG. 5B illustrates an isometric view of an anchor housing, in accordance with at least one example of this disclosure.
Figure 5C:
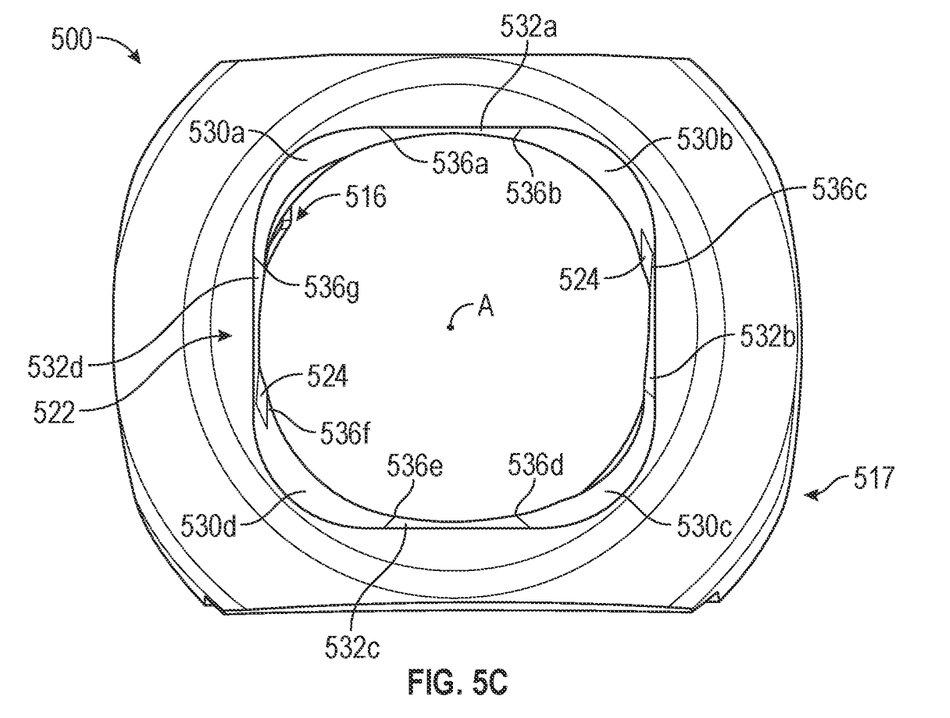
FIG. 5C illustrates a bottom view of an anchor housing, in accordance with at least one example of this disclosure.

FIG. 5A illustrates an isometric view of an anchor housing 500, in accordance with at least one example of this disclosure. FIG. 5B illustrates an isometric view of the anchor housing 500, in accordance with at least one example of this disclosure. FIG. 5C illustrates a bottom view of an anchor housing 500, in accordance with at least one example of this disclosure. The anchor housing 500 can be similar to those of anchor assemblies 100 and 400 above; however, FIGS. 5A-5C show additional details of the housing 500. FIGS. 5A-5C are discussed below concurrently.

The housing 500 can include a proximal portion 515, an anchor bore 516, a distal portion 517, a secondary bore 522, and helical grooves 524. The secondary bore 522 can include corner notches 530a-530d (first angled notch 530a, second angled notch 530b, third angled notch 530c, and fourth angled notch 530d), straight portions 532a-532d, and edges 536a-536g. Also shown in FIGS. 5A-5C are axis A, and orientation indicators Proximal, Distal, Medial, Lateral, Anterior, and Posterior.

In some examples, each of the corner notches 530a-530d can be connected by straight portions 532a-532d. In some examples, each of straight portions 532a-532d can be bevels of the secondary opening 522, each having a substantially flat or planar face. The first straight portion 532a can be connected to the first angled notch 530a and the second angled notch 530b, the second straight portion 532b can be connected to the second angled notch 530b and the third angled notch 530c, the third straight portion 532c can be connected to the third angled notch 530c and the fourth angled notch 530d, and the fourth straight portion 532d can be connected to the first angled notch 530a and the fourth corner notch 530d.

Each of the edges 536a-536g can each be located where each of the corner notches 530a-530d meets one of the straight portions 532a-532d. For example, the edge 536a can be a connection between the corner notch 530a and the straight portion 530a; and, the edge 536b can be the connection between the straight portion 532a and the corner notch 530b. In some examples, each of the straight portions 532a-532d can be positioned relative to the corner notches 530a-530d such that each of the edges 536a-536g can be configured to limit or minimize engagement of the edges 536a-536g with an anchor. That is, the straight portions 532a-532d can be positioned to limit radially inward extension of each of the edges 536a-536g from the secondary bore 522. This can help to promote smooth movement of the anchor between the corner notches 530a-530d. This can also help prevent relative movement of the anchor to the housing 500, because the contact between the anchor and the secondary bore 522 can be relatively consistent.

FIGS. 5A-5C also show that the helical grooves 524 can terminate near where straight portion 532a meets corner notch 530b and where straight portion 532d meets corner notch 530d (diagonally across for each other). Terminating the helical grooves 524 at these positions can help to limit interference of the helical grooves 524 with the secondary opening 522, which can help to simplify manufacturing and can help allow for desired angulation of the anchors with respect to the housing 500. However, the helical grooves 524 can also be placed relative to the secondary opening 5522 such that the head of the anchor can contact the helical grooves 524 to provide a sharp edge for contact with the head when the anchor is fully screwed into the bore and when the head applies a force on the housing 500. This can help prevented relative movement of the head to the housing 500 following installation of the anchor assembly.

Figure 6:
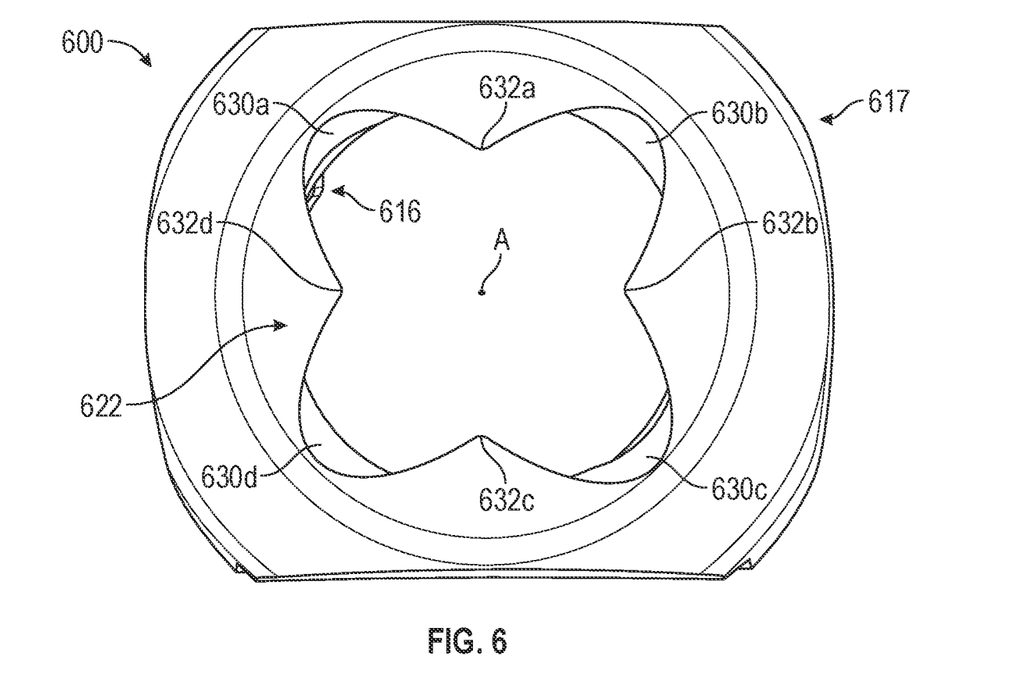
FIG. 6 illustrates a bottom view of an anchor housing, in accordance with at least one example of this disclosure.

FIG. 6 illustrates a bottom view of an anchor housing 600, in accordance with at least one example of this disclosure. Anchor housing 600 can include a secondary bore having a substantially cloverleaf shape configured to promote relatively high angulation of an anchor relative to the housing. Any of the previously discussed anchor assembly can be modified include a secondary bore having a substantially cloverleaf shape.

The housing 600 can include an anchor bore 616, a distal portion 617, and a secondary bore 622. The secondary bore 622 can include corner notches 630a-630d, and protrusions 632a-632d. Also shown in FIG. 6 are axis A, and orientation indicators Medial, Lateral, Anterior, and Posterior.

The housing 600 can be similar to other housing discussed above, such as housing 500, except that secondary bore 622 of housing 600 can have a substantially cloverleaf shape. That is, the corner notches 630a-630d can have a smaller radius of curvature than corner notches 530a-530d, in some examples (though a larger radius can be used in other examples). Further, the corner notches 630a-630d can be connected at protrusions 632a-632d instead of by straight portions. This shape can provide an anchor housing that biases an anchor to extreme angulations, which can be helpful during a procedure where a desired angulation is known prior to securing the anchor housing to the bone.

Figure 7:
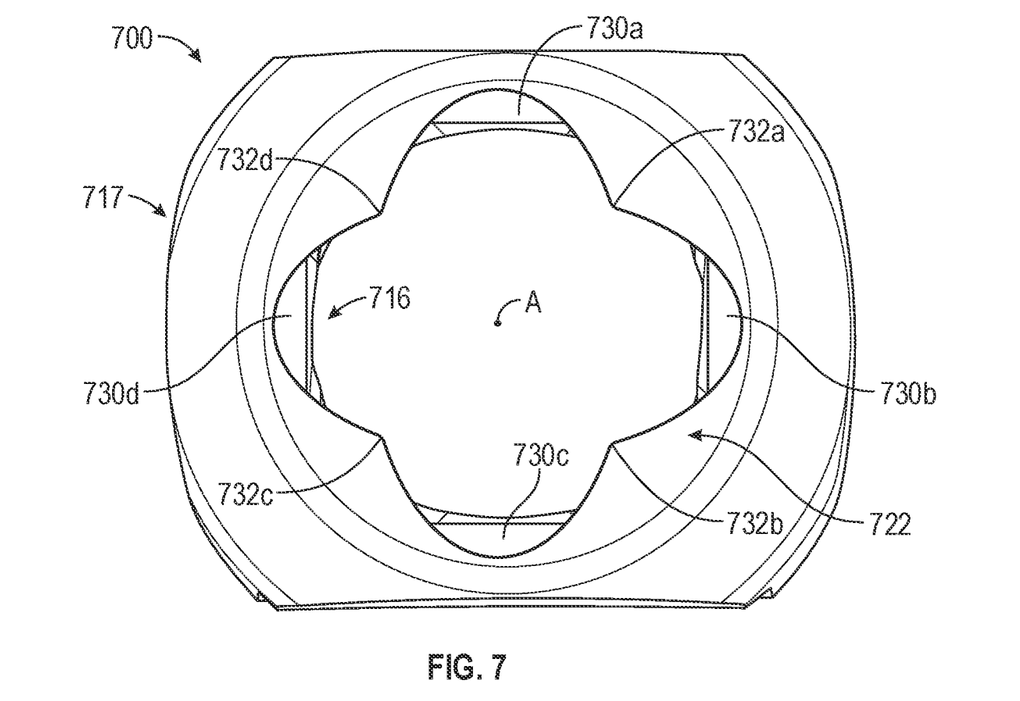
FIG. 7 illustrates a bottom view of an anchor housing, in accordance with at least one example of this disclosure.

FIG. 7 illustrates a bottom view of an anchor housing 700, in accordance with at least one example of this disclosure. Anchor housing 700 can include a secondary bore having a substantially cloverleaf shape configured to promote relatively high angulation of an anchor relative to the housing. Any of the previously discussed anchor assembly can be modified include a secondary bore having a substantially cloverleaf shape.

The housing 700 can include an anchor bore 716, a distal portion 717, and a secondary bore 722. The secondary bore 722 can include corner notches 730a-730d, and protrusions 732a-732d. Also shown in FIG. 7 are axis A, and orientation indicators Medial, Lateral, Anterior, and Posterior.

The anchor housing 700 can be similar to anchor housing 600 in that secondary opening 722 of the anchor housing 700 can have a substantially clover leaf shape. However, the secondary opening 722 of the anchor housing 700 can be rotated about 90 degrees (in one example) relative to the secondary opening 622 of the housing 600. This arrangement of housing 700 can provide high angulation in the anterior-posterior directions and can provide higher angulation in the lateral-medial directions, with respect to the orientation of FIG. 7. This can translate to relatively high angulation in the interior-superior (caudal-cranial) directions and to higher angulation in the lateral-medial directions with respect to a patient.

Also, the corner notches 730a-730d of the secondary opening of the anchor housing 700 can have a relatively larger radius of curvature than the corner notches 630a-630d of the housing 600. The larger radius of curvature can provide different angulation of the shank relative to the housing 700, allowing the housing 700 to be used in a larger variety of angulation applications.

Figure 8:
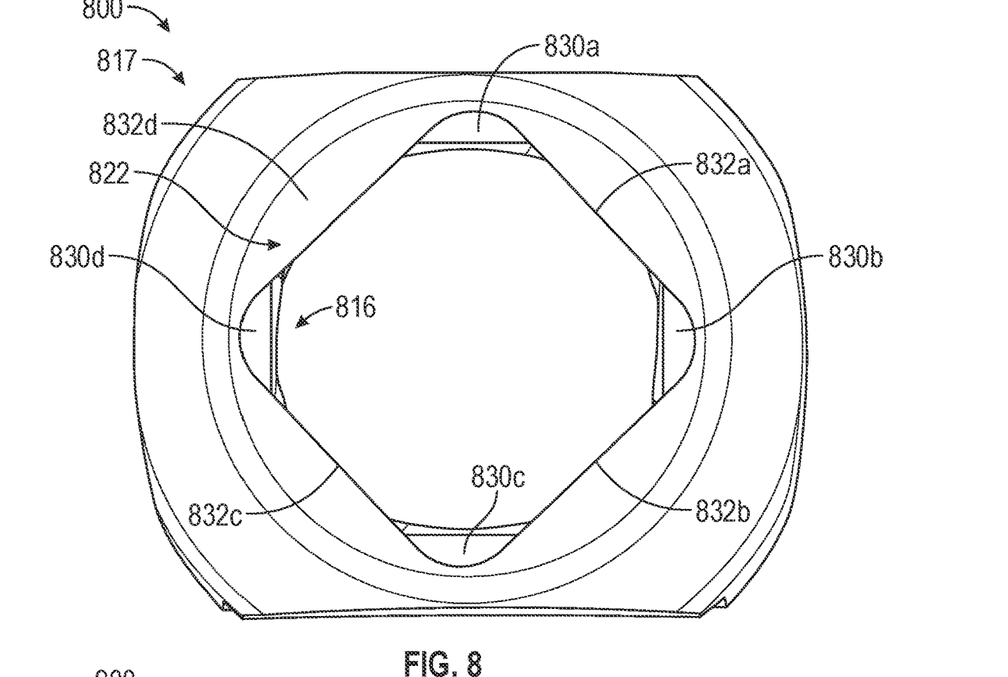
FIG. 8 illustrates a bottom view of an anchor housing, in accordance with at least one example of this disclosure.

FIG. 8 illustrates a bottom view of an anchor housing 800, in accordance with at least one example of this disclosure. The anchor housing 800 can include a secondary bore having a substantially diamond shape configured to promote relatively high angulation of an anchor relative to the housing in anterior, posterior, medial, and lateral directions. Any of the previously discussed anchor assembly can be modified include a secondary bore having a substantially diamond shape.

The housing 800 can include an anchor bore 816, a distal portion 817, and a secondary bore 822. The secondary bore 822 can include corner notches 830a-830d, and straight portions 832a-832d. Also shown in FIG. 8 are axis A, and orientation indicators Medial, Lateral, Anterior, and Posterior.

The anchor housing 800 can be similar to anchor housing 500 in that the secondary opening 822 of the anchor housing 800 can have a substantially geometric shape of a square with rounded corners. However, the secondary opening 822 of the anchor housing 800 can be rotated about 90 degrees (in one example) relative to the secondary opening 522 of the housing 500. This arrangement of housing 800 can provide high angulation in the anterior-posterior directions and can provide higher angulation in the lateral-medial directions with respect to the orientation of FIG. 8. This can translate to relatively high angulation in the interior-superior (or caudal-cranial) directions and to higher angulation in the lateral-medial directions, with respect to a patient.

The secondary opening 822 of the anchor housing 800 can also be similar to that of the anchor housing 700, except that the secondary opening 822 of the housing 800 includes straight portions 832a-832d connecting to corner notches 830a-830d. This can provide relatively smooth movement of the anchor between the corner notches 830a-830d.

Figure 9:
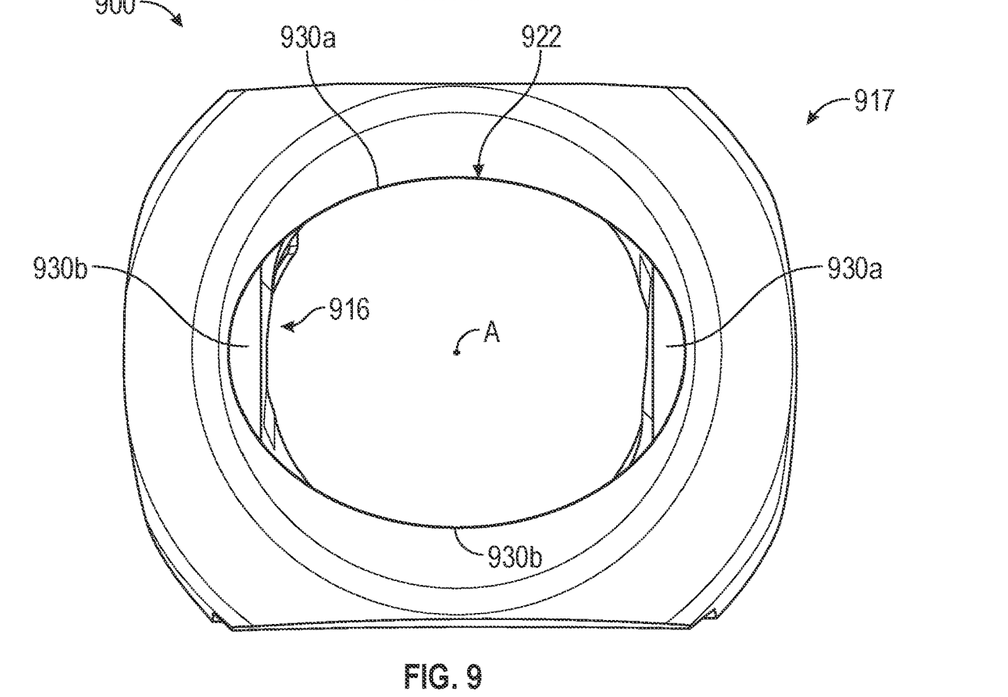
FIG. 9 illustrates a bottom view of an anchor housing, in accordance with at least one example of this disclosure.

FIG. 9 illustrates a bottom view of an anchor housing 900, in accordance with at least one example of this disclosure. Anchor housing 900 can include a secondary bore having a substantially ovalar shape configured to promote relatively high angulation of an anchor relative to the housing in medial and lateral directions. Any of the previously discussed anchor assembly can be modified include a secondary bore having a substantially ovalar shape.

The housing 900 can include an anchor bore 916, a distal portion 917, and a secondary bore 922. The secondary bore 922 can include corner notches 930a and 930b, and curved portions 932a and 932b. Also shown in FIG. 9 are axis A, and orientation indicators Medial, Lateral, Anterior, and Posterior.

FIG. 9 can be similar to the other housings discussed above, except that the secondary opening 922 can have an ovalar shape. More specifically, the secondary opening 922 can include two corner notches 930a and 930b connected by two curved portions 932a and 932b. The corner notches 930a and 930b can provide relatively large angulation of an anchor with respect to the housing 900 medially-to-laterally and the curved portions 932a and 932b can provide less extreme angulation of the anchor superiorly-to-inferiorly with respect to the housing.

In other examples, oval can be rotated 90 degrees such that the secondary opening is configured to provide extreme angulation of the anchor with respect to the housing 900 in anterior and posterior directions with respect to the orientation of FIG. 9, which can translate to high angulation in inferior and superior directions when the housing 900 is secured to a patient, in some procedures.

NOTES AND EXAMPLES

The following, non-limiting examples, detail certain aspects of the present subject matter to solve the challenges and provide the benefits discussed herein, among others.

Example 1 is an anchor assembly couplable to bone, the assembly comprising: an anchor comprising: a shank securable to bone; and a head coupled to a proximal portion of the shank; and a housing comprising: a proximal portion including an anchor bore extending distally into the housing along a longitudinal axis of the housing, the anchor bore configured to retain the head of the anchor therein; and a distal portion including a secondary bore configured to engage the anchor to limit angulation of the anchor relative to the housing, the secondary bore comprising: a first portion configured to limit the angulation of the anchor to a first angle relative to the longitudinal axis; and a plurality of second portions each configured to limit the angulation of the anchor to a second angle relative to the longitudinal axis that is greater than the first angle.

In Example 2, the subject matter of Example 1 optionally includes wherein the secondary bore is positioned at a distal end of the distal portion, and wherein the secondary bore is substantially coaxial with the anchor bore and the longitudinal axis.

In Example 3, the subject matter of any one or more of Examples 1-2 optionally include wherein each of the plurality of second portions each is configured to receive the shank therein and to create a desired angular trajectory for the shank in reference to the housing.

In Example 4, the subject matter of any one or more of Examples 1-3 optionally include wherein the secondary bore has a geometric shape substantially of a square with rounded corners from a distal perspective.

In Example 5, the subject matter of any one or more of Examples 1-4 optionally include wherein the first portion is defined by a first chafer extending radially outward from the secondary bore, wherein each of the plurality of second portions are defined by a plurality of bevels extending radially outward, and wherein each of the plurality of bevels curves along a face of each of the plurality of bevels.

In Example 6, the subject matter of any one or more of Examples 1-5 optionally include wherein the secondary bore comprises a plurality of first portions including the first portion, each of the plurality of second portions connected by the plurality of first portions.

In Example 7, the subject matter of Example 6 optionally includes wherein each of the plurality of first portions is substantially planar.

In Example 8, the subject matter of Example 7 optionally includes wherein the shank is threaded and wherein housing includes a helical groove configured to receive the threaded shank therethrough.

In Example 9, the subject matter of Example 8 optionally includes wherein the helical groove terminates substantially at connection between one of the plurality of first portions and one of the plurality of second portions.

In Example 10, the subject matter of any one or more of Examples 6-9 optionally include wherein the plurality of first portions and plurality of second portions are arranged symmetrically about a sagittal plane and a coronal plane of the housing.

In Example 11, the subject matter of any one or more of Examples 2-10 optionally include wherein the anchor further comprises a neck including a neck diameter that is smaller than a diameter of the shank and a diameter of the head, and wherein contact between the neck and the housing Is configured to limit the angulation of the anchor to the second angle relative to the longitudinal axis.

In Example 12, the subject matter of any one or more of Examples 2-11 optionally include wherein the housing includes two open sides, each open side substantially forming a U shape configured to receive a connecting member therethrough.

In Example 13, the subject matter of any one or more of Examples 1-12 optionally include the assembly further comprising: a lower piston disposable in the central bore and configured to engage the head; an upper piston disposable in the bore and configured to support a connecting member; and a biasing element disposable between the lower piston and the upper piston to bias the upper piston away from the lower piston.

Example 14 is an anchor housing configured to receive an anchor therethrough, the anchor couplable to a bone, the anchor housing comprising: a proximal portion including an anchor bore extending distally into the housing along a longitudinal axis of the housing, the anchor bore configured to receive a shank of an anchor therethrough and configured to retain a head of the anchor therein; and a distal portion including a secondary opening configured to engage the anchor to limit angulation of the anchor relative to the housing, the secondary bore comprising: a substantially planar face configured to limit the angulation of the anchor to a first angle relative to the longitudinal axis; and an angled notch configured to limit the angulation of the anchor to a second angle relative to the longitudinal axis that is greater than the first angle.

In Example 15, the subject matter of Example 14 optionally includes wherein the distal portion further comprises a second angled notch connected to the first angled notch by the substantially planar face, the second angled notch configured to limit the angulation of the anchor to a third angle relative to the longitudinal axis that is greater than the first angle.

In Example 16, the subject matter of Example 15 optionally includes wherein the distal portion further comprises a third angled notch and a fourth angled notch, the third angled notch and the fourth angled notch configured to limit the angulation of the anchor to a third angle and a fourth angle, respectively, relative to the longitudinal axis that are greater than the first angle.

In Example 17, the subject matter of Example 16 optionally includes wherein the distal portion further comprises a second substantially planar face, a third substantially planar face, and a fourth substantially planar face, the first substantially planar face connected to the first angled notch and the second angled notch, the second substantially planar face connected to the second angled notch and the third angled notch, the third substantially planar face connected to the third angled notch and the fourth angled notch, and the fourth substantially planar face connected to the first angled notch and the fourth angled notch.

In Example 18, the subject matter of any one or more of Examples 16-17 optionally include wherein the first substantially planar face is connected to the first angled notch defining a first edge and the second angled notch is connected to the first substantially planar face defining a second edge, wherein the first substantially planar face is connected to the first angled notch and the second angled notch to limit engagement of the first edge and the second edge with the anchor.

In Example 19, the subject matter of any one or more of Examples 17-18 optionally include wherein a first segment of the first substantially planar face and a third segment of the third substantially planar face are substantially parallel, and wherein a second segment of the second substantially planar face and a fourth segment of the fourth substantially planar face are substantially parallel.

Example 20 is an anchor housing couplable to a bone, the housing comprising: a proximal portion including an anchor bore extending distally into the housing along a longitudinal axis of the housing, the anchor bore configured to receive the shank therethrough and configured to retain the head of the anchor therein; and a distal portion including a secondary bore configured to engage the anchor to limit angulation of the anchor relative to the housing, the secondary bore comprising: a first portion configured to limit the angulation of the anchor to a first angle relative to the longitudinal axis; and a second portion configured to limit the angulation of the anchor to a second angle relative to the longitudinal axis that is greater than the first angle.

In Example 21, the systems, devices, or methods of any one or any combination of Examples 1-20 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including"

and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An anchor assembly couplable to bone, the assembly comprising:
   an anchor comprising:
   a shank; and
   a head connected to the shank; and
   a housing comprising:
   a proximal portion defining an anchor bore extending along a longitudinal axis and configured to retain the head of the anchor therein; and
   a distal portion including a secondary bore having a geometric shape substantially of a square with rounded corners from a distal perspective, the anchor bore and secondary bore enabling polyaxial movement of the anchor relative to a longitudinal axis of the housing, the distal portion comprising:
   a plurality of first portions, each configured to engage the anchor to limit the angulation of the anchor to a first angle relative to the longitudinal axis; and
   a plurality of second portions defined by rounded corner chamfers, each second portion configured to engage the anchor to limit the angulation of the anchor to a second angle relative to the longitudinal axis that is greater than the first angle to provide different degrees of angulation of the shank relative to the housing for use in a cortical trajectory.

2. The anchor assembly of claim 1, wherein the first and second angles are greater than zero, wherein the secondary bore has a bore size less than a size of the head to inhibit passage of the head through the secondary bore in response to polyaxial rotation of the anchor relative to the housing, wherein the secondary bore is located at a distal end of the distal portion, and wherein the secondary bore is substantially coaxial with the anchor bore and the longitudinal axis.

3. The anchor assembly of claim 1, wherein the plurality of first portions and plurality of second portions are disposed in the secondary bore symmetrically relative to the longitudinal axis and wherein the plurality of first portions is defined by a first chamfer extending radially outward from the secondary bore, and wherein each of rounded corner chamfers extend radially outward from the secondary bore.

4. The anchor assembly of claim 3, wherein the secondary bore comprises a plurality of first portions including the first portion, each of the plurality of second portions connected by the plurality of first portions.

5. The anchor assembly of claim 4, wherein each of the plurality of first portions is defined by a straight chamfer.

6. The anchor assembly of claim 5, wherein the shank is threaded and wherein housing includes a helical groove configured to receive the threaded shank therethrough.

7. The anchor assembly of claim 6, wherein the helical groove terminates substantially at connection between one of the plurality of first portions and one of the plurality of second portions.

8. The anchor assembly of claim 6, wherein the plurality of first portions and plurality of second portions are arranged symmetrically about a sagittal plane and a coronal plane of the housing.

9. The anchor assembly of claim 1, wherein the anchor further comprises a neck including a neck diameter that is smaller than a diameter of the shank and a diameter of the head, and wherein contact between the neck and the housing is configured to limit the angulation of the anchor to the second angle relative to the longitudinal axis.

10. The anchor assembly of claim 1, the anchor assembly further comprising:
    a lower piston disposable in the anchor bore and configured to engage the head;
    an upper piston disposable in the anchor bore and configured to support a connecting member; and
    a biasing element disposable between the lower piston and the upper piston to bias the upper piston away from the lower piston.

11. An anchor assembly couplable to bone, the anchor assembly comprising:
    an anchor comprising a shank, a head, and a neck connected to the head and shank; and
    a housing comprising:
    an anchor bore extending along a longitudinal axis and configured to receive the head of the anchor therein; and
    a secondary bore having a geometric shape substantially of a square with rounded chamfers from a distal perspective and comprising:
    a plurality of first portions each configured to engage the neck to limit angulation of the anchor to a first nonzero angle relative to the longitudinal axis; and
    a plurality of rounded corners connected to and positioned between adjacent first portions, each of the plurality of rounded corners being sized to receive the neck to limit the angulation of the anchor to a second nonzero angle relative to the longitudinal axis that is greater than the first nonzero angle.

12. The anchor assembly of claim 11, wherein the plurality of first portions and the plurality of rounded corners are arranged symmetrically about a sagittal plane and a coronal plane of the housing.

13. The anchor assembly of claim 11, wherein the anchor bore and secondary bore are configured to enable polyaxial rotation of the anchor relative to the longitudinal axis, wherein the secondary bore is located at a distal end of a distal portion of the housing, and wherein the secondary bore is substantially coaxial with the anchor bore and the longitudinal axis.

14. The anchor assembly of claim 11, wherein, to enable polyaxial movement of the anchor relative to the longitudinal axis of the housing, the plurality of rounded corners are located substantially equidistant from the longitudinal axis, the plurality of first portions are located substantially equidistant from the longitudinal axis, and the plurality of rounded corners are further from the longitudinal axis than the plurality of first portions, and wherein each of the plurality of first portions is defined by a straight chamfer.

15. The anchor assembly of claim 14, wherein each of the rounded corners is defined by a rounded chamfer, the rounded chamfers connected to the straight chamfers to together define the secondary bore.

16. The anchor assembly of claim 15, wherein the secondary bore has a secondary bore size less than a size of the head to inhibit passage of the head through the secondary bore in response to movement of the anchor relative to the housing and wherein each straight chamfer is substantially planar.

17. An anchor assembly couplable to bone, the anchor assembly comprising:
an anchor comprising a shank, a head, and a neck connected to the head and shank; and
a housing comprising:
an anchor bore extending along a longitudinal axis and configured to receive the head of the anchor therein; and
a secondary bore comprising:
a plurality of straight chamfers each configured to engage the shank to limit angulation of the anchor to a first angle relative to the longitudinal axis; and
a plurality of rounded chamfers connected to the straight chamfers, the plurality of rounded chamfers each sized to receive the neck to limit the angulation of the anchor to a second angle relative to the longitudinal axis that is greater than the first angle to provide different degrees of angulation of the shank relative to the housing for use in a cortical trajectory, wherein the anchor bore and secondary bore are each configured to enable polyaxial rotation of the anchor relative to the longitudinal axis, and wherein the plurality of straight chamfers and the plurality of rounded chamfers are arranged symmetrically about a sagittal plane and a coronal plane of the housing.

18. The anchor assembly of claim 17, wherein the secondary bore has a geometric shape substantially of a square with rounded chamfers from a distal perspective.

19. The anchor assembly of claim 17, wherein each of the straight chamfers is configured to engage the neck and wherein each of the straight chamfers is substantially planar.

20. The anchor assembly of claim 19, wherein the shank is threaded and wherein housing includes a helical groove configured to receive the threaded shank therethrough, the helical groove terminating substantially at a connection between one of the straight chamfers and one of the rounded chamfers.

* * * * *